(12) United States Patent
Kinoshita et al.

(10) Patent No.: US 8,471,053 B2
(45) Date of Patent: Jun. 25, 2013

(54) PROCESS AND APPARATUS FOR PRODUCTION OF CYANOHYDRIN COMPOUND, AND PROCESS FOR PRODUCTION OF α-HYDROXYESTER COMPOUND

(75) Inventors: Yuichiro Kinoshita, Isumi (JP); Naoki Fujiwara, Isumi (JP); Kazuya Nakagawa, Toyama (JP); Koji Midorikawa, Tokyo (JP)

(73) Assignee: Nippoh Chemicals Co., Ltd., Tokyo (JP)

( * ) Notice: Subject to any disclaimer, the term of this patent is extended or adjusted under 35 U.S.C. 154(b) by 403 days.

(21) Appl. No.: 12/734,258

(22) PCT Filed: Oct. 21, 2008

(86) PCT No.: PCT/JP2008/068997
§ 371 (c)(1),
(2), (4) Date: Apr. 21, 2010

(87) PCT Pub. No.: WO2009/054355
PCT Pub. Date: Apr. 30, 2009

(65) Prior Publication Data
US 2010/0261929 A1 Oct. 14, 2010

(30) Foreign Application Priority Data

Oct. 23, 2007 (JP) ................... 2007-275695

(51) Int. Cl.
*C07C 253/08* (2006.01)
(52) U.S. Cl.
USPC ........................................ 558/351
(58) Field of Classification Search
USPC ........................................ 558/351
See application file for complete search history.

(56) References Cited

U.S. PATENT DOCUMENTS

| | | | |
|---|---|---|---|
| 4,987,256 A | 1/1991 | Ebata et al. | 564/126 |
| 5,122,462 A | 6/1992 | Miethe | |
| 2005/0271572 A1 | 12/2005 | Benderly | |
| 2006/0111586 A1 | 5/2006 | Schladenhauffen | |
| 2008/0214861 A1 | 9/2008 | Kozono | |
| 2009/0082587 A1 | 3/2009 | Schladenhauffen | |
| 2009/0304569 A1 | 12/2009 | Benderly | |

FOREIGN PATENT DOCUMENTS

| | | | |
|---|---|---|---|
| DE | 40 08 411 | | 9/1991 |
| GB | 892781 | | 3/1962 |
| JP | 34-522 B | | 2/1959 |
| JP | 35-5755 B | | 5/1960 |
| JP | 36-5869 B | | 5/1961 |
| JP | 36-11965 B | | 7/1961 |
| JP | 36-12115 B | | 7/1961 |
| JP | 10-25273 | | 1/1998 |
| JP | 2003-192655 | | 7/2003 |
| JP | 2003-192655 A | * | 7/2003 |
| JP | 2007-55953 A | | 3/2007 |

OTHER PUBLICATIONS

Del Rosso et al. "Pilot Plant Tests for Glyoxal Production: Reactor Thermal Behavior" React. Kinet. Catal. Lett., 1992, vol. 48, pp. 655-661.*
Chen et al. "A Practical High Through-Put Continuous Process for the Synthesis of Chiral Cyanohydrins" Journal of Organic Chemistry, 2002, vol. 67, pp. 8251-8253.*
Petran Chen, et al., "Journal of Organic Chemistry," Shanghai Institute of Organic Chemistry, 2002, vol. 67, No. 23, p. 8251-8253.
Takamura, et al. (2002) "Efficient synthesis of antihyperglycemic (S)-α-Aryloxy-β-phenylpropionic acid using a bifuntional asymmetric catalyst" Chem. Pharm. Bull. 50(8):1118-1121.
Thomson Scientific, (2007) Database WPI, XP-002665385 (Abstract).
EP Search Report for Application No. 08841132.7 dated Dec. 16, 2011.

* cited by examiner

*Primary Examiner* — Joseph Kosack
(74) *Attorney, Agent, or Firm* — Harness, Dickey & Pierce, P.L.C.

(57) ABSTRACT

A process according to the present invention for producing a cyanohydrin compound flow-reacts a carbonyl compound with hydrogen cyanide in the presence of a catalyst, and can therefore reduce the residence time. This makes it possible to reduce the period of time over which the resulting cyanohydrin compound is exposed to an unreacted portion of the carbonyl compound. As a result, the resulting cyanohydrin compound can be prevented from reacting with the unreacted portion. This makes it possible to produce the cyanohydrin compound in good yield. That is, the process according to the present invention for producing a cyanohydrin compound produces a cyanohydrin compound in good yield from a carbonyl compound and hydrogen cyanide.

8 Claims, 1 Drawing Sheet

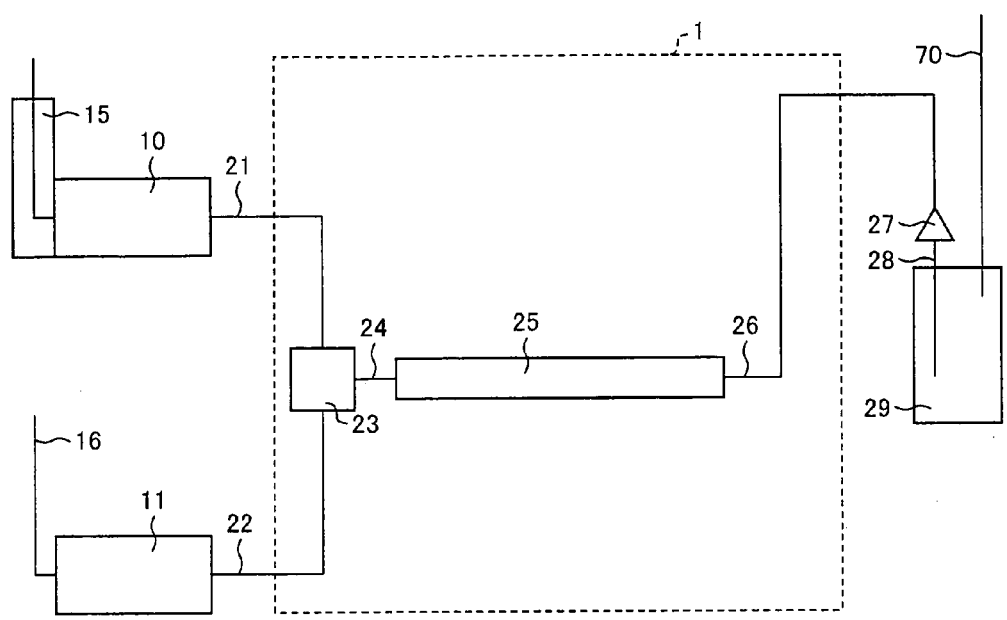

PROCESS AND APPARATUS FOR PRODUCTION OF CYANOHYDRIN COMPOUND, AND PROCESS FOR PRODUCTION OF α-HYDROXYESTER COMPOUND

TECHNICAL FIELD

The present invention relates to apparatuses and processes for producing cyanohydrin compounds and processes for producing α-hydroxyester compounds and, in particular, to a process and apparatus for producing a cyanohydrin compound from a carbonyl compound and hydrogen cyanide and to a process for producing an α-hydroxyester compound with use of such a cyanohydrin compound.

BACKGROUND ART

There have been known processes for producing cyanohydrin compounds by reacting carbonyl compounds such as aldehyde compounds and ketones with hydrogen cyanide. Cyanohydrin compounds are useful as starting materials for synthesis of various compounds, e.g., for production of α-hydroxyester compounds, and various production processes have been developed for efficient production (Patent Literatures 1 to 7).

Conventionally, in particular, the development of a process for producing a cyanohydrin compound with use of a ketone has been advanced. As a process for producing a cyanohydrin compound with use of a ketone, Patent Literature 8 discloses a process for producing a deuterated cyanohydrin compound by reacting deuterated acetone with hydrogen cyanide.

In Patent Literature 8, deuterated acetone and hydrogen cyanide react with each other in a flow reactor to form a deuterated cyanohydrin compound that is high in rate of deuteration. The flow reactor is a reactor system into which the reactants are continuously introduced to react with each other and out of which the reaction product is discharged. By reacting deuterated acetone with hydrogen cyanide in such a flow reactor, a decrease in rate of deuteration of the deuterated cyanohydrin compound is prevented.

In producing a cyanohydrin compound with use of an aldehyde compound, a production process including the step of introducing hydrogen cyanide into a batch reactor containing an aldehyde compound in advance has conventionally been used. A reaction that involves the use of a batch reactor is sometimes referred to as "batch process", by which the reactants are introduced into the reactor at a time and the reaction product is taken out after the reaction comes to equilibrium or after a certain rate of reaction is achieved. Such a process for producing a cyanohydrin compound with use of an aldehyde compound is disclosed in Patent Literature 1. In Patent Literature 1 a cyanohydrin compound is produced by introducing, into a reactor containing an aldehyde compound in advance, hydrogen cyanide gas diluted with inert gas.

Citation List
Patent Literature 1
Japanese Patent Application Publication, Tokukosho, No. 34-522 B (Publication Date: Feb. 9, 1959)
Patent Literature 2
Japanese Patent Application Publication, Tokukosho, No. 35-5755 B (Publication Date: May 25, 1960)
Patent Literature 3
Japanese Patent Application Publication, Tokukosho, No. 36-5869 B (Publication Date: May 26, 1961)
Patent Literature 4
Japanese Patent Application Publication, Tokukosho, No. 36-11965 B (Publication Date: Jul. 29, 1961)
Patent Literature 5
Japanese Patent Application Publication, Tokukosho, No. 36-12115 B (Publication Date: Jul. 31, 1961)
Patent Literature 6
Japanese Patent Application Publication, Tokukosho, No. 38-6761 B (Publication Date: May 22, 1963)
Patent Literature 7
Japanese Patent Application Publication, Tokukaihei, No. 10-25273 A (Publication Date: Jan. 27, 1998)
Patent Literature 8
Japanese Patent Application Publication, Tokukai, No. 2007-55953 A (Publication Date: Mar. 8, 2007)

SUMMARY OF INVENTION

The reaction between a carbonyl compound and hydrogen cyanide in production of a cyanohydrin compound is an exothermic reaction. Moreover, because the reaction between a carbonyl compound and hydrogen cyanide is very high in speed and therefore very high in calorific value per unit time. Therefore, a cyanohydrin compound has been produced by feeding a carbonyl compound into a reactor and then introducing hydrogen cyanide into the reactor slowly in accordance with the speed of heat removal. However, there has been such a problem that a slow and prolonged reaction of hydrogen cyanide with a carbonyl compound leads to a decrease in reaction yield of a cyanohydrin compound that is produced by the reaction. Further, introduction of hydrogen cyanide at a speed higher than the speed of heat removal leads to an abnormal rise in temperature of the reaction liquid, thus entailing risks such as evaporation and dispersion of hydrogen cyanide, as well as facilitating decomposition of the cyanohydrin compound.

The present invention has been made in view of the foregoing problems, and it is an object of the present invention to provide: a process for producing a cyanohydrin compound without a decrease in yield by reacting a carbonyl compound with hydrogen cyanide; and a process for producing an α-hydroxyester compound with use of a cyanohydrin compound produced thereby.

As a result of their diligent study to solve the foregoing problems, the inventors have newly found that especially when a cyanohydrin compound is industrially produced, prolonged exposure of the cyanohydrin compound in the presence of a carbonyl compound causes a decrease in yield of the cyanohydrin compound. That is, the inventors have found that a decrease in yield of the cyanohydrin compound can be prevented by using a high heat-removal efficiency flow reactor to reduce the residence time between introducing the materials into the reactor for them to start to react with each other and taking the reaction product out of the reactor. Based on these findings, the inventors have finally accomplished the present invention.

That is, a process according to the present invention for producing a cyanohydrin compound is a process for producing a cyanohydrin compound from a carbonyl compound (excluding a deuteride) and hydrogen cyanide, the process including performing a flow reaction between the carbonyl compound and the hydrogen cyanide in the presence of a catalyst.

Further, an apparatus according to the present invention for producing a cyanohydrin compound is an apparatus for producing a cyanohydrin compound from a carbonyl compound (excluding a deuteride) and hydrogen cyanide, the apparatus including: a reactor in which to perform a flow reaction between a carbonyl compound and hydrogen cyanide in the presence of a catalyst; a first introducer through which the carbonyl compound is introduced into the tubular reactor; and a second introducer through which the hydrogen cyanide is introduced into the tubular reactor.

The process thus arranged and the apparatus thus structured makes it possible to greatly reduce the residence time between introducing the carbonyl compound and the hydrogen cyanide into the reactor for them to start to react with each other and taking the reaction product out of the reactor, as compared with the residence time in a reaction in which the batch process is used. This makes it possible to reduce the period of time over which the resulting cyanohydrin compound is exposed to an unreacted portion of the carbonyl compound in the reaction system, and to therefore produce the cyanohydrin compound in good yield by preventing the resulting cyanohydrin compound from reacting with the unreacted portion. The term "residence time" here means the time between introducing the raw materials into the reactor for them to start to react with each other and taking the reaction product out of the reactor. Further, in the present invention, the reaction system refers to a system that is used between (a) starting the reaction by mixing the carbonyl compound and the hydrogen cyanide together and (b) stopping the reaction by either isolating the cyanohydrin compound or neutralizing or removing the basic catalyst, or that is used in a reaction in the next step.

Further, the flow reaction between the carbonyl compound and the hydrogen cyanide results in higher heat removal efficiency than does a reaction system using the batch process. Therefore, even if a high temperature is reached instantaneously, it is possible to remove heat efficiently. This makes it possible to prevent a decrease in yield due to decomposition of the resulting cyanohydrin compound.

Furthermore, in the process according to the present invention for producing a cyanohydrin compound, it is preferable that the carbonyl compound be an aldehyde compound represented by general formula (1).

Further, in the process according to the present invention for producing a cyanohydrin compound, it is preferable that the carbonyl compound (excluding a deuteride) be an aldehyde compound represented by general formula (1):

[Chem. 1]

(1)

wherein $R^1$ is an aryl group or a C1-C10 hydrocarbon group; and $R^1$ is allowed to have a substituent therein and to contain an atom other than carbon in a structure thereof.

The process thus arranged makes it possible to greatly reduce the residence time between introducing the aldehyde compound and the hydrogen cyanide into the reactor for them to start to react with each other and taking the reaction product out of the reactor, as compared with the residence time in a reaction in which the batch process is used. This makes it possible to reduce the period of time over which the resulting cyanohydrin compound is exposed to an unreacted portion of the aldehyde compound in the reaction system, and to therefore produce the cyanohydrin compound in good yield by preventing the resulting cyanohydrin compound from reacting with the unreacted portion.

Further, the flow reaction between the aldehyde compound and the hydrogen cyanide results in higher heat removal efficiency than does a reaction system using the batch process. Therefore, even if a high temperature is reached instantaneously, it is possible to remove heat efficiently. This makes it possible to prevent a decrease in yield due to decomposition of the resulting cyanohydrin compound.

Further, in the process according to the present invention for producing a cyanohydrin compound, it is preferable that the flow reaction between the carbonyl compound and the hydrogen cyanide be performed in a tubular reactor. This makes it possible to perform the flow reaction between the carbonyl compound such as the aldehyde compound and the hydrogen cyanide efficiently in a simple structure. This makes it possible, as a result, to prevent prolonged exposure of the resulting cyanohydrin compound to an unreacted portion of the carbonyl compound such as the aldehyde compound.

Furthermore, in the process according to the present invention for producing a cyanohydrin compound, it is preferable that the tubular reactor has a fluid channel whose short side ranges from 0.01 mm to 15 mm in length. This makes it possible to efficiently remove heat generated by the reaction between the carbonyl compound such as the aldehyde compound and the hydrogen cyanide. As a result, decomposition of the resulting cyanohydrin compound can be inhibited, and the speed of a reaction of the cyanohydrin compound with an unreacted portion of the aldehyde compound can be slowed down.

Further, in the process according to the present invention for producing a cyanohydrin compound, it is preferable that residence time during the flow reaction be not more than 1,000 seconds. This makes it possible to greatly reduce the residence time, as compared with a reaction system using the general batch process. This makes it possible to prevent prolonged exposure of the resulting cyanohydrin compound to an unreacted portion of the carbonyl compound such as the aldehyde compound. This makes it possible, as a result, to produce the cyanohydrin compound in good yield by preventing the resulting cyanohydrin compound from reacting with the unreacted portion.

Further, in the process according to the present invention for producing a cyanohydrin compound, it is preferable that the hydrogen cyanide be flow-reacted in a proportion of 0.9 to 3.0 mol with respect to 1 mol of the carbonyl compound. This makes it possible to cause the carbonyl compound such as the aldehyde compound and the hydrogen cyanide to react efficiently with each other, and to therefore prevent an unreacted portion of the carbonyl compound such as the aldehyde compound from remaining in the reaction system.

Furthermore, in the process according to the present invention for producing a cyanohydrin compound, it is preferable that the catalyst be at least either an organic basic compound or an inorganic basic compound, and it is more preferable that the catalyst be a compound selected from the group consisting of an amine compound, an aromatic amine compound, an alkali metal compound, a metal alkoxide compound, and an alkaline-earth metal compound. Further, it is preferable that the flow reaction be performed in the presence of 0.01 to 0.1 mol of the catalyst with respect to 1 mol of the hydrogen cyanide. This makes it possible to produce the cyanohydrin compound in good yield by facilitating the reaction between the carbonyl compound such as the aldehyde compound and the hydrogen cyanide.

A process according to the present invention for producing an α-hydroxyester compound includes the step of hydrolyzing and esterifying a cyanohydrin compound produced by a production process according to the present invention.

The process thus arranged makes it possible to obtain an intermediate, i.e. a cyanohydrin compound in good yield, in producing an α-hydroxyester compound by using a carbonyl compound such as an aldehyde compound as a starting material, and to therefore obtain the α-hydroxyester compound in good yield.

Additional objects, features, and strengths of the present invention will be made clear by the description below. Further, the advantages of the present invention will be evident from the following explanation in reference to the drawings.

BRIEF DESCRIPTION OF DRAWINGS

FIG. 1 is a schematic diagram describing a reaction apparatus that is used in a production process according to the present invention.

REFERENCE SIGNS LIST

1 Water bath
10 Pump
11 Pump
15 Introducer (second introducer)
16 Introducer (first introducer)
23 Mixer
24 Introducing pipe
25 Reactor (tubular reactor)
26 Introducing pipe
27 Back-pressure regulating valve
28 Reaction liquid discharge line
29 Reaction liquid collecting container
70 Exhaust vent

DESCRIPTION OF EMBODIMENTS

An embodiment of the present invention is described below in detail.

[Process for Producing a Cyanohydrin Compound]

A process according to the present invention for producing a cyanohydrin compound includes performing a flow reaction between a carbonyl compound (excluding a deuteride) such as an aldehyde compound represented by general formula (1) and hydrogen cyanide in the presence of a catalyst:

[Chem. 2]

(1)

wherein $R^1$ is an aryl group or a C1-C10 hydrocarbon group; and $R^1$ is allowed to have a substituent therein and to contain an atom other than carbon in a structure thereof.

In the present invention, the carbonyl compound only needs to be a compound having a carbonyl group and excluding a deuteride thereof, and examples of the carbonyl compound include aldehyde compounds and ketone compounds. Further, in the present invention, the aldehyde compound is a compound having an aldehyde group within a molecule, and the cyanohydrin compound is a compound having a cyano group and a hydroxyl group within a molecule. The present invention has as an object, in particular, to produce a cyanohydrin compound (α-cyanohydrin) having a cyano group and a hydroxyl group both attached to an identical carbon atom.

Since examples of the carbonyl compound in the production process according to the present invention include aldehyde compounds as mentioned above, the aldehyde compounds are described first.

(Aldehyde Compound)

Those aldehyde compounds which are used in the present invention are carbonyl compounds, represented by general formula (1), which have at least one hydrogen atom in a carbonyl group thereof (i.e., which have a formyl group). The inventors have found that when an aldehyde compound or, in particular, one having a small carbon number is used in producing a cyanohydrin compound by reacting the aldehyde compound with hydrogen cyanide, the resulting cyanohydrin compound is prone to react with an unreacted portion of the aldehyde compound and therefore low in reaction yield. Therefore, the present invention brings about a particularly significant effect when that one of the aforementioned aldehyde compounds which has a small carbon number is used.

That is, the present invention makes it possible to produce a cyanohydrin compound in good yield by reacting an aldehyde compound having a small carbon number or, in particular, one having a C1-C3 hydrocarbon group with hydrogen cyanide. Those aldehyde compounds which are used in the present invention are preferably aldehyde compounds that are small in carbon number, and examples of such aldehyde compounds include, but are not limited to: saturated alkylaldehydes such as formaldehyde, acetoaldehyde, and propionaldehyde; unsaturated alkylaldehydes such as acrylaldehyde, methacrylaldehyde, and propiolaldehyde; and aromatic aldehydes such as benzaldehyde, naphthoaldehyde, phthalaldehyde, and nicotinaldehyde. Further, these aldehyde compounds may have a substituent such as amine, amide, methoxy, phenyl, nitro, hydroxyl, aldehyde, or carboxylic acid. When an aldehyde compound that is used in the present invention is solid at ambient temperature, it is possible to use the aldehyde compound after dissolving or suspending it in a solvent that is inactive against the reaction.

(Ketone Compound)

Other than aldehyde compounds, examples of the carbonyl compound in the production process according to the present invention include ketone compounds. Ketone compounds that can be used in the present invention only need to have a ketone group, and examples of such ketone compounds include acetone, 2-butanone, 2-pentanone, 3-methyl-2-butanone, 3-pentanone, 3-hexanone, 2-methyl-3-pentanone, 3-heptanone, 2-methyl-3-hexanone, 2,4-dimethyl-3-pentanone, acetophenone, 2-nonanone, 2-octanone, 2-heptanone, 2-hexanone, 4-methyl-2-pentanone, 4-heptanone, cyclohexanone, and 2,6-dimethyl-4-heptanone.

(Hydrogen Cyanide)

As the hydrogen cyanide that is used in the present invention, (a) hydrogen cyanide obtained by the ammonium oxidization of methane, (b) hydrogen cyanide produced by acidifying lithium cyanide, sodium cyanide, potassium cyanide, calcium cyanide, or the like with hydrochloric acid or sulfuric acid, or (c) hydrogen cyanide purified by distilling either (a) or (b) can be used. Further, because the hydrogen cyanide is unstable, it is possible to use hydrogen cyanide containing an acidic stabilizer such as sulfur dioxide.

(Catalyst)

As the catalyst that is used in the production process according to the present invention, a basic catalyst is used. As the basic catalyst, either an organic basic compound or an inorganic basic compound can be used. Among them, the organic basic compound is preferred. Examples of those compounds which are used as the catalyst include: tertiary amino compounds such as trimethylamine, triethylamine, tripropylamine, triisopropylamine, tributylamine, triheptylamine, trioctylamine, 1,4-diazabicyclo[2,2,2]octane, N-methylpyrrolidine, N-methylpiperidine, N-methylmorpholine, and N,N-dimethylaniline; metal alcoholate compounds such as lithium methoxide, lithium ethoxide, lithium propoxide, lithium butoxide, sodium methoxide, sodium ethoxide, sodium propoxide, sodium butoxide, potassium methoxide, potassium ethoxide, potassium propoxide, and potassium butoxide; alkali metal compounds and alkaline-earth metal compounds such as lithium hydroxide, sodium hydroxide, potassium hydroxide, calcium hydroxide, magnesium hydroxide, lithium carbonate, sodium carbonate, potassium carbonate, calcium carbonate, and magnesium carbonate; and basic compounds such as basic ion-exchange resin and zeolite.

It is preferable that the proportion of such a catalyst that is introduced into a reactor be 0.001 to 0.1 mol, more preferably 0.003 to 0.05 mol, or even more preferably 0.005 to 0.01 mol with respect to 1 mol of the hydrogen cyanide. It is undesirable that the proportion of the catalyst that is introduced into the reactor be less than 0.001 mol with respect to 1 mol of the hydrogen cyanide, because when the proportion is less than 0.001 mol, the reaction between the carbonyl compound such as the aldehyde compound and the hydrogen cyanide slows down to the extent that the reaction is not completed within the residence time. On the other hand, it is undesirable that the proportion of the catalyst be greater than 0.1 mol, because when the proportion is greater than 0.1 mol, that large portion of the catalyst which was not used in the reaction remains in the reactor and polymerization of the hydrogen cyanide tends to take place.

Further, when the hydrogen cyanide that is used contains an acidic stabilizer, the reaction between the basic compound and the acidic stabilizer may cause loss of catalytic activity. In order to prevent such loss, it is only necessary to add to the basic compound in an amount equivalent in number of contained moles to the stabilizer. The proportion of the catalyst is an effective amount of the catalyst after such offsetting. When the basic compound is solid at room temperature, it is only necessary to use the basic compound after dissolving or suspending it either in the carbonyl compound such as the aldehyde compound or in the solvent.

(Solvent)

In the production process according to the present invention, it is possible to use the solvent that is inactive to the reaction between the carbonyl compound such as the aldehyde compound and the hydrogen cyanide. When the carbonyl compound, such as the aldehyde compound, which is used as a raw material, the basic compound, which is used as the catalyst, or the cyanohydrin compound, which is the product, is solid at reaction temperature, it is possible to use these substances after dissolving or suspending them in the solvent.

Usable examples of the solvent in the present invention include: aliphatic hydrocarbon solvents such as pentane, hexane, heptane, and octane; alicyclic hydrocarbon solvents such as cyclopentane, cyclohexane, cycloheptane, and cyclooctane; aromatic hydrocarbon solvents such as benzene, toluene, and xylene; halogenated hydrocarbon solvents such as dichloromethane, chloroform, tetrachloromethane, dichloroethane, and chlorobenzene; and ether solvents such as diethyl ether, diisopropyl ether, methyl-t-butyl ether, dibutyl ether, and tetrahydrofuran. In the case of use of, e.g., toluene as a solvent in producing an α-hydroxyester compound with use of a cyanohydrin compound produced by the present invention, it is preferable to use toluene as a solvent also in producing the cyanohydrin compound.

The amount of the solvent that is used only needs to be appropriately either such an amount that the carbonyl compound, such as the aldehyde compound, which is used as a raw material, the basic compound, which is used as the catalyst, or the cyanohydrin compound, which is the product, can be dissolved, or such an amount that a solution in which these substances have been suspended exhibits fluidity.

(Reaction)

In the production process according to the present invention, the reaction between the carbonyl compound and the hydrogen cyanide is a reaction represented by reaction formula (2), when explained by taking as an example the aldehyde compound represented by general formula (1), in which the cyanohydrin compound is produced through the addition to the aldehyde compound represented by general formula (1) of hydrogen cyanide activated by the catalyst.

[Chem. 3]

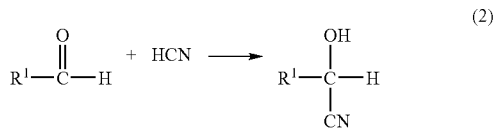

wherein $R^1$ is an aryl group or a C1-C10 hydrocarbon group; and $R^1$ is allowed to have a substituent therein and to contain an atom other than carbon in a structure thereof.

The reaction represented by reaction formula (2) is an exothermic reaction. Especially when the cyanohydrin compound is produced on an industrial scale, the reaction calorie per unit time becomes so extremely high that the temperature of the reaction liquid is likely to abnormally rise. In this case, there are such problems that the resulting cyanohydrin compound becomes prone to be decomposed; therefore, it is necessary to control the calorie. In order to inhibit heat from being generated in the reaction system and sufficiently remove heat from the reaction system, it is necessary to react the aldehyde compound with the hydrogen cyanide slowly over a prolonged period. However, when a prolonged period is required for the reaction, there is such a problem that the reaction of the resulting cyanohydrin compound with an unreacted portion of the aldehyde compound leads to a decrease in reaction yield of the cyanohydrin compound.

The production process according to the present invention flow-reacts the carbonyl compound such as the aldehyde compound with the hydrogen cyanide in the presence of the catalyst, and can therefore reduce the residence time. As a result, a reaction of the resulting cyanohydrin compound with an unreacted portion of the carbonyl compound such an aldehyde compound can be prevented by preventing prolonged exposure of the resulting cyanohydrin compound to the unreacted portion. This makes it possible to produce the cyanohydrin compound in good yield.

The term "residence time" here means the time between introducing the raw materials (the carbonyl compound such as the aldehyde compound and the hydrogen cyanide) into the reactor for them to start to react with each other and taking the reaction product out of the reactor, and may be expressed as the reaction time of the flow reaction in the reaction system.

The "flow reaction" here means a reaction in which the reactant fluid compounds are continuously introduced into the reactor to react with each other and the reaction product is discharged out of the system. The production process according to the present invention makes it possible to prevent prolonged exposure of the resulting cyanohydrin compound to an unreacted portion of the carbonyl compound such as the aldehyde compound because in the production process the carbonyl compound such as the aldehyde compound and the hydrogen cyanide are continuously introduced into the reactor for them to react with each other and the resulting cyanohydrin compound is discharged out of the reaction system.

The reactor in which to perform the flow reaction between the carbonyl compound such as the aldehyde compound and the hydrogen cyanide is not particularly limited, and may be of any structure as long as it is a flow reactor into which the fluids can be continuously introduced to react with each other and out of which the reaction product can be discharged. That is, the reactor that is used in the present invention only needs to be a reactor having an inlet through which the reactant fluids are introduced, an outlet through which the reaction product is discharged, and a space where the fluids thus introduced react with each other in the system.

Further, because the speed of the reaction between the carbonyl compound such as the aldehyde compound and the hydrogen cyanide is very high, these substances immediately react with each other, once they are introduced into the reactor, to produce the cyanohydrin compound. Therefore, the production of the cyanohydrin compound on an industrial scale can be realized by keeping on introducing the carbonyl compound such as the aldehyde compound and the hydrogen cyanide continuously into the reactor for use in the reaction.

Further, in the production process according to the present invention, the flow reaction between the carbonyl compound such as the aldehyde compound and the hydrogen cyanide may be performed in a tubular reactor. This makes it possible, as a result, to perform the flow reaction between the carbonyl compound such as the aldehyde compound and the hydrogen cyanide efficiently in a simple structure. This makes it possible to prevent prolonged exposure of the resulting cyanohydrin compound to an unreacted portion of the carbonyl compound such as the aldehyde compound. Such a tubular reactor may be of any structure as long as it is a reactor into which two or more types of reactant gas or liquid fluid can be continuously introduced to react with each other. Suitably usable examples of such a tubular reactor include a plate reactor, a tube and shell reactor, and a spiral reactor. Such a reactor is sometimes referred to as "heat exchanger" or "reaction heat remover" because of its high heat exchange efficiency. Therefore, the reactor may be in the shape of a circular, angular, or elliptical tube in cross-section. In particular, it is preferable to use a tubular reactor called a microreactor whose pipe diameter is as very small as in the order of micrometers.

Furthermore, it is preferable that the tubular reactor, in which the flow reaction between the carbonyl compound such as the aldehyde compound and the hydrogen cyanide is performed, have a fluid channel whose short side ranges from 0.01 mm to 15 mm in length. This makes it possible to efficiently remove heat generated by the reaction between the carbonyl compound such as the aldehyde compound and the hydrogen cyanide. As a result, decomposition of the resulting cyanohydrin compound can be inhibited, and a reaction of the cyanohydrin compound with an unreacted portion of the carbonyl compound such as the aldehyde compound can be prevented. Further, because such a small-diameter tubular reactor as mentioned above can be made easily and inexpensively to withstand pressure, the reaction can be performed more safely even at high temperatures and pressures in the reaction system.

Such a tubular reactor only needs to have a fluid channel whose short side ranges from 0.01 mm to 15 mm in length, and the short side of the cross-section from the inlet to the output of the tubular reactor does not need to be constant. It is undesirable that the short side of the channel be less than 0.01 mm in length, because when the short side of the channel is less than 0.01 mm in length, high pressure is required for the movement of the fluids thus introduced. It is undesirable that the short side of the channel be greater than 15 mm in length, because when the short side of the channel is greater than 15 mm in length, there are a decrease in heat removal efficiency and a decrease in reaction efficiency of the fluids. Further, the long side of the channel is not particularly limited, and the long side of the cross-section from the inlet to the output of the tubular reactor does not need to be constant. When the fluid channel of the tubular reactor is in the shape of a cylinder, the short side of the fluid channel is equal to the pipe diameter (inside diameter) of the tubular reactor.

The rate of flow in the reactor that is used in the present invention only needs to be appropriately changed in accordance with the speed of the reaction between the carbonyl compound such as the aldehyde compound and the hydrogen cyanide, and as such, only needs to be set so that the reaction liquid residence time (reaction time) falls within a range of preferably less than 1,000 seconds, more preferably 500 seconds, or even more preferably 0.01 to 200 seconds. The reaction residence time in the reactor during the flow reaction can be adjusted by appropriately changing the length of the reactor and the flow rates of the raw materials.

Further, in the present invention, it is preferable that the maximum temperature inside of the reactor in which to perform the flow reaction between the carbonyl compound such as the aldehyde compound and the hydrogen cyanide fall within a range of $-10$ to 300° C., more preferably 0 to 250° C., even more preferably 10 to 200° C. Because the temperature inside of the reactor partially increases due to heat generated by the reaction and then decreases due to heat removal treatment, the temperature inside of the reactor during the residence time is not constant. Therefore, the maximum temperature inside of the reactor indicates a maximum temperature that is attained during the residence time, and the period of time over which this temperature is maintained can be approximately several seconds.

It is undesirable that the maximum temperature inside of the reactor be lower than $-10°$ C., because at such a low temperature there is an extreme decrease in reaction speed in some substrates. Moreover, for the temperature inside of the reactor to be lower than $-10°$ C., a high-performance freezing machine is required; furthermore, such a low temperature cannot be attained unless the reactant raw materials are finely divided and then fed into the reactor. Therefore, it is not realistic to attain such a low temperature. On the other hand, it is undesirable that the maximum temperature inside of the reactor be higher than 300° C., because at such a high temperature there occurs decomposition of raw materials and products in some substrates. Moreover, for the temperature inside of the reactor to be higher than 300° C., an increase in size of a reaction apparatus is required for the sake of safety.

The pressure inside of the reactor that is used in the present invention may be normal, but it is preferable that the reactor be internally pressurized by providing a back-pressure regulating valve. It is preferable that the reaction pressure inside of the reactor fall within a range of 0 to 10 MPa, more preferably 0.1 to 5 MPa, even more preferably 0.2 to 1 MPa. It is undesirable that the reaction pressure inside of the reactor be below the range, because at such a low reaction pressure there may be a decrease in heat removal efficiency due to vaporization of the hydrogen cyanide and the carbonyl compound such as the aldehyde compound. On the other hand, it is undesirable that the reaction pressure inside of the reactor be above the range, because it costs a tremendous amount of money to build such a high-pressure apparatus and the rise in maximum reaction temperature due to an elevation in boiling point of the reaction product makes the control of production of a by-product difficult.

The temperature inside of the reactor that is used in the present invention may be regulated from the outside of the reactor by immersing the reactor in a water bath and appropriately regulating the temperature of the water bath. Alternatively, the temperature inside of the reactor may be regulated from the outside of the reactor by providing a tube or the like around the reactor and allowing a liquid (refrigerant) whose temperature has been appropriately regulated to flow through the tube. Usable examples of the refrigerant that is used include: coolant water chilled by a cooling tower; and a refrigerant (an aqueous solution of ethylene glycol and calcium chloride) chilled by use of a freezing machine. The use of a high heat-removal efficiency reactor and the reduction in residence time make it possible to suitably use a wide-temperature-range refrigerant.

The reactor may be equipped with a measuring instrument for appropriately measuring the temperature of the reaction liquid inside of the reactor. The reactor is preferably equipped with a plurality of such measuring instruments, in particular, so that the temperature can be measured, for example, immediately after introduction of the raw material substances such as the carbonyl compound such as the aldehyde compound and the hydrogen cyanide and immediately after mixing of these substances.

It is preferable that the reactor that is used in the present invention be made of a material that does not react with substances for use in a reaction or substances that are produced by the reaction, and examples of such a material include: metals such as iron, copper, titanium, and nickel; various alloys such as stainless steel, Monel, Hastelloy, and Incoloy; resins (fluoroplastics); glass; and china (cordierite, ceramics).

In the production process according to the present invention, it is preferable that the proportion of the hydrogen cyanide to the carbonyl compound such as the aldehyde compound to be flow-reacted with each other be 0.9 to 3.0 mol, more preferably 1.0 to 2.0 mol, or even more preferably 1.0 to 1.5 mol with respect to 1 mol of the carbonyl compound such as the aldehyde compound. The carbonyl compound such as the aldehyde compound and the hydrogen cyanide may be introduced either en bloc or in parts. That is, it is only necessary that the carbonyl compound such as the aldehyde compound and the hydrogen cyanide that are introduced into the reactor between the beginning and the end of the residence time fall within the respective molar quantity ranges, regardless of the proportion of the hydrogen cyanide to the carbonyl compound such as the aldehyde compound to be flow-reacted with each other.

Because the proportion of the hydrogen cyanide to the carbonyl compound such as the aldehyde compound in the reactor during the flow reaction is such that they are substantially equal in molar quantity as stated above, the carbonyl compound such as the aldehyde compound and the hydrogen cyanide react with each other so efficiently that an unreacted portion of the carbonyl compound such as the aldehyde compound or the hydrogen cyanide can be prevented from remaining in the reactor. It is undesirable that the proportion of the hydrogen cyanide be less than 0.9 mol with respect to 1 mol of the carbonyl compound such as the aldehyde compound, because such a small proportion of the hydrogen cyanide causes a large amount of an unreacted portion of the carbonyl compound such as the aldehyde compound to remain in the reactor and therefore leads to a decrease in yield of the cyanohydrin compound. On the other hand, it is undesirable that the proportion of the hydrogen cyanide be greater than 3.0 mol, because such a large proportion of the hydrogen cyanide causes a large amount of an unreacted portion of the hydrogen cyanide to remain in the reactor and therefore causes such problems that an recovery operation is required and that the remaining hydrogen cyanide is polymerized.

A cyanohydrin compound obtained by the process according to the present invention for producing a cyanohydrin compound may be either purified by a publicly known method such as distillation or column chromatography or used as it is without purification in a reaction such as synthesis of an α-hydroxyester compound.

A cyanohydrin compound that is produced by the process according to the present invention for producing a cyanohydrin compound is an organic compound having a cyanide ion added to the carbonyl group of the carbonyl compound such as the aldehyde compound, and sometimes referred to as "cyanhydrin compound". Examples of cyanohydrin compounds that can be suitably produced by the present invention include, but are not limited to: saturated alkylhydroxynitriles such as hydroxyacetonitrile, lactonitrile, and α-hydroxybutanenitrile; unsaturated alkylhydroxynitriles such as α-hydroxybuta-3-ennitrile, α-hydroxy-3-methylbuta-3-ennitrile, and α-hydroxybuta-3-innitrile; aromatic alkylhydroxynitriles such as mandelonitrile, hydroxy(2-naphthyl)acetonitrile, (3-(cyano(hydroxy)methyl)phenyl))(hydroxy)acetonitrile, and hydroxy(pyridine-3-yl)acetonitrile. Further, these cyanohydrin compounds may have a substituent such as amine, amide, methoxy, phenyl, nitro, hydroxyl, aldehyde, or carboxylic acid. In the process according to the present invention for producing a cyanohydrin compound, α-hydroxybutyronitrile can be produced, for example, by performing a flow reaction between propionaldehyde and hydrogen cyanide in the presence of a catalyst.

The process according to the present invention for producing a cyanohydrin compound makes it possible to produce a cyanohydrin compound in a reaction yield of not less than 95%. Further, when a cyanohydrin compound is produced on an industrial scale, e.g., when a cyanohydrin compound is produced by a reaction in an amount of approximately not less than 500 g/min, the cyanohydrin compound can be produced in a reaction yield higher than the reaction yield, in particular, of a cyanohydrin compound that is produced by a reaction system using the conventional batch process.

In the present invention, the carbonyl compound such as the aldehyde compound flow-reacts with the hydrogen cyanide; therefore, the residence time can be reduced. This makes it possible to reduce the period of time over which the resulting cyanohydrin compound is exposed to an unreacted portion of the carbonyl compound such as the aldehyde compound, and to therefore produce the cyanohydrin compound in good yield by preventing the resulting cyanohydrin compound from reacting with the unreacted portion. Further, the present invention also makes it possible to efficiently remove heat generated by the reaction between the carbonyl compound such as the aldehyde compound and the hydrogen cyanide. Furthermore, the present invention makes it possible to perform the reaction in a space narrower than the space in a reaction system using the conventional batch process. Therefore, the process according to the present invention for producing a cyanohydrin compound can be suitably used, in particular, to produce a cyanohydrin compound on an industrial scale.

[Process for Producing an α-hydroxyester Compound]

The present invention also provides a process for producing an α-hydroxyester compound with use of a cyanohydrin compound produced by the production process according to the present invention. The process according to the present invention for producing an α-hydroxyester compound includes the steps of: (i) producing a cyanohydrin compound by the process according to the present invention for producing a cyanohydrin compound; and (ii) hydrolyzing and esterifying the cyanohydrin compound thus produced.

When explained by taking as an example the aldehyde compound represented by general formula (1), the reaction in the step (i) is represented by reaction formula (2), and the reaction in the step (ii) is represented, for example, by reaction formula (3):

[Chem. 4]

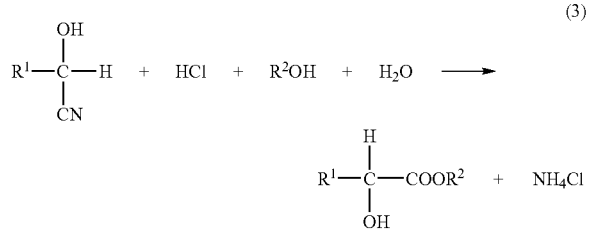

(3)

wherein $R^1$ and $R^2$ are independently an aryl group or a C1-C10 hydrocarbon group; and $R^1$ or $R^2$ is allowed to have a substituent therein and to contain an atom other than carbon in a structure thereof.

That is, the cyanohydrin compound can be hydrolyzed and esterified efficiently by introducing hydrochloric gas into a mixture of the cyanohydrin compound, alcohols, water, and a solvent. Examples of alcohols that can be used in this reaction include methanol, ethanol, n-propanol, i-propanol, n-butanol, s-butanol, n-heptanol, n-hexanol, n-octanol, 2-ethylhexanol, cyclohexanol, and benzyl alcohol. In the present invention, methanol, ethanol, n-propanol, i-propanol, and the like can be suitably used. Further, the reaction in the step (ii) is not limited to reaction formula (3) as long as it is a reaction in which the cyanohydrin compound can be hydrolyzed and esterified.

Ester compounds that can be suitably produced by the process according to the present invention for producing an ester compound are carboxylic acid esters that are produced by a reaction between carboxylic acid obtained from a cyanohydrin compound and alcohol, and examples of such esters include, but are not limited to: saturated alkylhydroxyesters such as methyl hydroxyacetate, methyl α-hydroxypropionate, and methyl α-hydroxybutyrate; unsaturated alkylhydroxyesters such as methyl α-hydroxybutenoate, methyl β-methyl-α-hydroxybutenoate, and methyl α-hydroxybutynoate; and aromatic hydroxyesters such as methyl mandelate, methyl hydroxy-2-naphthylacetate, methyl hydroxy(3-(1-hydroxy-2-methoxy-2-oxoethyl))phenylacetate, and methyl hydroxy(pyridine-3-yl)acetate. Further, these ester compounds may have a substituent such as amine, amide, methoxy, phenyl, nitro, hydroxyl, aldehyde, or carboxylic acid.

In the process according to the present invention for producing an α-hydroxyester compound, for example, with use of α-hydroxybutyronitrile produced by the process for producing a cyanohydrin compound, methyl α-hydroxybutyrate can be produced by hydrolyzing α-hydroxybutyronitrile and esterifying it with methanol.

The process according to the present invention for producing an α-hydroxyester compound makes it possible to produce an α-hydroxyester compound with use of a cyanohydrin compound produced in good yield. Therefore, when the α-hydroxyester compound is produced by using an equimolar amount of a carbonyl compound such as an aldehyde compound as a starting material, the α-hydroxyester compound can be produced in good yield in comparison with the conventional process. This makes it possible to realize a reduction in production cost of the α-hydroxyester compound.

[Apparatus for Producing a Cyanohydrin Compound]

Furthermore, the present invention provides an apparatus for producing a cyanohydrin compound from a carbonyl compound such as an aldehyde compound represented by general formula (1) and hydrogen cyanide. The apparatus according to the present invention for producing a cyanohydrin compound includes: a reactor in which to perform a flow reaction between a carbonyl compound such as an aldehyde compound and hydrogen cyanide in the presence of a catalyst; a first introducer through which the aldehyde compound is introduced into the reactor; and a second introducer through which the hydrogen cyanide is introduced into the reactor.

[Chem. 5]

(1)

wherein $R^1$ is an aryl group or a C1-C10 hydrocarbon group; and $R^1$ is allowed to have a substituent therein and to contain an atom other than carbon in a structure thereof.

An apparatus according to the present invention for producing a cyanohydrin compound is described with reference to FIG. 1. FIG. 1 is a schematic diagram describing an apparatus according to the present invention for producing a cyanohydrin compound. As shown in FIG. 1, the reaction apparatus includes a reactor (tubular reactor) 25 and introducers (first and second introducers) 15 and 16 through which a carbonyl compound such as an aldehyde compound and hydrogen cyanide are introduced, respectively. The reactor 25 of the production apparatus according to the present invention is identical in structure to the reactor used in the production process according to the present invention.

Moreover, to the reactor 25, a mixer 23 for mixing the raw material substances may be connected through an introducing pipe 24. Such a mixer 23 only needs to be able to mix two or more types of fluid separately introduced thereinto, and suitably usable examples of such a mixer include a Y-shaped mixer, T-shaped mixer, a cruciform mixer, a pipeline mixer, a screw-feeder mixer, and a micromixer. The production apparatus according to the present invention may either include a mixer 23 separated from the reactor 25 or include a mixer 23 integrated with the reactor 25. In the case of use of a mixer 23 separated from the reactor 25, the reactor 25 and the mixer 23 are connected through an introducing pipe 24 such as a tube so that a liquid can be transferred. Moreover, the temperature inside of the reactor 25 and the mixer 23 may be externally regulated by immersing them in a water bath 1 and then appropriately regulating the temperature of the water bath 1.

Further, the introducers 15 and 16, through which the raw materials are introduced, are connected to the mixer 23 through introducing pipes (tubes) 21 and 22 so that the raw material substances are introduced into the mixer 23 from the introducers 15 and 16, respectively. Each of the first and second introducers 15 and 16 of the production apparatus of the present invention only needs to be an introducer through which to introduce either one of the raw materials from which a cyanohydrin compound is produced, namely either the carbonyl compound such as the aldehyde compound or the hydrogen cyanide. In the production apparatus according to the present invention, there may be provided a plurality of such first and second introducers 15 and 16, then the raw materials from which a cyanohydrin compound is produced can be introduced separately in several batches. In such a case, there may be provided as many inlets (not shown) through which the raw materials are introduced into the reactor 25 or the mixer 23 and as many introducing pipes (tubes) 21 and 22 as the first and second introducers 15 and 16.

These introducers 15 and 16 may be equipped with liquid transfer pumps 10 and 11, respectively, for transferring the reactant raw material substances into the reactor 25 or the mixer 23. Moreover, the pressure inside of a reaction system including the reactor 25 and the mixer 23 may be regulated by the liquid transfer pumps 10 and 11, which transfer the reactants.

The carbonyl compound such as the aldehyde compound and the hydrogen cyanide, which have been introduced into the reactor 25 or the mixer 23 through the respective introducers 15 and 16, react with each other in the reactor 25 to produce a cyanohydrin compound. The production apparatus according to the present invention may include a reaction liquid collecting container 29 for collecting the cyanohydrin compound produced in the reactor 25. Further, the production apparatus according to the present invention may include a raw material recovery container (not shown) for recovering those portions of the reactant raw material substances which have passed unreacted through the reactor 25. The reaction liquid collecting container 29 and the raw material recovery container are connected to the reactor 25 through an introducing pipe 26 such as a tube and a reaction liquid discharge line 28 so that a liquid can be transferred. There may be provided a back-pressure regulating valve 27 between the introducing pipe 26 and the reaction liquid discharge line 28.

Further, the production apparatus according to the present invention may be equipped with a measuring instrument (not shown) for appropriately measuring the temperature of the reaction liquid inside of the reactor. The production apparatus may be equipped with a plurality of such measuring instruments, in particular, so that the temperature can be measured, for example, immediately after introduction of the raw material substances (e.g., the carbonyl compound such as the aldehyde compound and the hydrogen cyanide) into the reactor 25 or the mixer 23 and immediately after mixing of these substances in the reactor 25 or the mixer 23. Furthermore, to the reaction liquid collecting container 29, an exhaust vent 70 may be connected.

Use of an apparatus according to the present invention for producing a cyanohydrin compound makes it possible to achieve a reduction in residence time, because the apparatus introduces a carbonyl compound such as an aldehyde compound and hydrogen cyanide into a reactor for them to react with each other. This makes it possible to reduce the period of time over which the resulting cyanohydrin compound is exposed to an unreacted portion of the carbonyl compound such as the aldehyde compound, and to therefore prevent the resulting cyanohydrin compound from reacting with the unreacted portion. As a result, the cyanohydrin compound can be produced in good yield without a decrease in reaction yield.

EXAMPLES

The present invention is described below in concrete terms with reference to Examples; however, the present invention is not limited to these Examples.

Example 1

In the present example, hydroxybutyronitrile was produced by use of such a reaction apparatus as shown in FIG. 1. To an HPLC pump (manufactured by Shimadzu Corporation) 10, an introducing pipe (outside diameter 1/16 in., inside diameter 0.5 mm; made of SUS316) 15 having a cooling section (not shown) was connected for liquefied hydrogen cyanide to be introduced. The cooling section (not shown) had a refrigerant of approximately −10° C. circulated therethrough so that a head portion of the HPLC pump 10 was cooled down to approximately 5° C. Further, to an HPLC pump (manufactured by Shimadzu Corporation) 11, an introducing pipe (outside diameter 1/16 in., inside diameter 0.5 mm; made of SUS316) 16 was connected for propionaldehyde (with a purity of not less than 98%) to be introduced. In the propionaldehyde, 0.6 mol % of triethylamine (with respect to aldehyde) had been dissolved in advance as a catalyst.

Furthermore, in order for the liquefied hydrogen cyanide to be introduced into the mixer (1/16 in., three-way union; manufactured by Swagelok) 23, the pump 10 and the mixer 23 were connected through a tube (outside diameter 1/16 in., inside diameter 0.5 mm) 21 made of SUS316. Similarly, in order for the 0.6 mol % propionaldehyde to be introduced into the mixer 23, the pump 11 and the mixer 23 were connected through a tube (outside diameter 1/16 in., inside diameter 0.5 mm) 22 made of SUS316.

Further, to an outlet of the mixer 23, a tube (outside diameter 1/16 in., inside diameter 0.5 mm) made of SUS316 was connected to serve as the tubular reactor 25. The length of this tubular reactor 25 was appropriately changed so that the reaction liquid residence time (5 to 180 seconds) was a predetermined period of time. Moreover, the tubular reactor 25 was equipped with a thermocouple so that the temperature of the reaction liquid immediately after the introduction of the raw materials from the mixer 23 into the tubular reactor 25 was able to be measured.

To the tubular reactor 25, a reaction liquid collecting container 29 was coupled through an introducing pipe 26 and a reaction liquid discharge line 28; and between the introducing pipe 26 and the reaction liquid discharge line 28, a back-pressure regulating valve 27 was provided. Further, into the reaction liquid collecting container 29, hydrochloric acid (of not less than 100 mol % of triethylamine to be introduced) for quenching triethylamine was introduced in advance. Moreover, to the reaction liquid collecting container 29, an exhaust vent 70 was connected. Further, the mixer 23 and the tubular reactor 25 were immersed in a water bath whose temperature had been adjusted to 30 to 60° C. The pressure inside of the reaction system was 0.4 MPa.

This reaction apparatus was used to produce hydroxybutyronitrile (HBN) by reacting propionaldehyde with liquefied hydrogen cyanide in the presence of triethylamine. The length of the tubular reactor 25 and the flow rates of the raw materials transferred by the pumps 10 and 11 were changed so that the average residence time of reaction liquids in the tubular reactor 25 varied from 5 to 180 seconds and the molar ratio of the raw materials supplied (i.e., the molar ratio of propionaldehyde to hydrogen cyanide) varied from 0.97 to 1.28:1.00, whereby the reaction yield of HBN in different reaction conditions was examined. HBN produced by each separate reaction was collected in the reaction liquid collecting container 29. A reaction liquid was analyzed in each separate condition, whereby the reaction yield of HBN was obtained. The results are shown in Table 1.

TABLE 1

| Reaction Condition | Average residence time (seconds) | HCN/nPA (mol/mol) | Water bath temperature (° C.) | Pressure inside of the system (MPa) | HBN yield (mol %) |
|---|---|---|---|---|---|
| 1 | 5 | 1.03 | 30 | 0.4 | 99 |
| 2 | 10 | 1.00 | | | 100 |
| 3 | 10 | 0.97 | | | 95 |
| 4 | 15 | 1.00 | | | 97 |
| 5 | 30 | 1.03 | | | 99 |
| 6 | 45 | 1.00 | | | 93 |
| 7 | 90 | 1.01 | | | 94 |
| 8 | 90 | 1.28 | | | 98 |
| 9 | 180 | 1.00 | | | 97 |
| 10 | 90 | 1.09 | 40 | | 94 |
| 11 | 10 | 1.03 | 60 | | 98 |

In Table 1, the molar ratio of propionaldehyde (nPA) to hydrogen cyanide (HCN) is denoted by HCN/nPA (mol/mol). In Reaction Conditions 1 to 11 listed in Table 1, amounts of HBN production varied from 1 to 5 g/min and reaction liquid temperatures immediately after introduction varied from 2 to 4° C. plus the water bath temperature. As shown in Table 1, the flow reactions between propionaldehyde and liquefied hydrogen cyanide together with triethylamine in the tubular reactor 25 resulted in as high reaction yields of HBN as 93 to 100 mol %, regardless of reaction condition such as average residence time.

In the present example and each of the examples below, the reaction yield of HBN is denoted by the amount (mol %) of HBN production based on the amount of aldehyde that is used in the reaction, and was calculated according to an absolute calibration method. The analysis condition was as follows: Column Inertsil CN-3 (4.6×250 mm 5 μm); Column temperature: 40° C.; Mobile phase Hexane:EtOH=95:5; Flow rate: 1.0 mL/min; Detector: RI (refractive index detector); Range: 8; Response: 5; Injection volume: 20 μL (fixed by a loop).

Example 2

In the present example, the reaction yield of HBN obtained when the amount of HBN production was scaled up was examined. Also in the present example, HBN was produced by use of such a reaction apparatus as shown in FIG. 1.

To a pump (C-610; manufactured by BUCHI) 10, an introducing pipe (outside diameter ⅛ in., inside diameter 2.17 mm; made of SUS316) 15 having a cooling section (not shown) was connected for liquefied hydrogen cyanide to be introduced. The cooling section (not shown) had a refrigerant of approximately –10° C. circulated therethrough so that a head portion of the HPLC pump 10 was cooled down to approximately 5° C. Further, to a pump (C-610; manufactured by BUCHI) 11, an introducing pipe (outside diameter ⅛ in., inside diameter 2.17 mm; made of SUS316) 16 was connected for propionaldehyde (with a purity of not less than 98%) to be introduced. In the propionaldehyde, 0.6 mol % of triethylamine had been dissolved in advance as a catalyst.

Furthermore, in order for the liquefied hydrogen cyanide to be introduced into the mixer (⅛ in., three-way union; manufactured by Swagelok) 23, the pump 10 and the mixer 23 were connected through a tube (outside diameter ⅛ in., inside diameter 2.17 mm) 21 made of SUS316. Similarly, in order for the propionaldehyde to be introduced into the mixer 23, the pump 11 and the mixer 23 were connected through a tube (outside diameter ⅛ in., inside diameter 2.17 mm) 22 made of SUS316.

Further, to an outlet of the mixer 23, a tube (outside diameter ⅛ in., inside diameter 2.17 mm) made of SUS316 was connected to serve as the tubular reactor 25. The tubular reactor 25 had thermocouples so provided in several places thereon as to monitor the temperature of a reaction liquid. To the tubular reactor 25, a reaction liquid collecting container 29 was coupled through an introducing pipe 26 and a reaction liquid discharge line 28; and between the introducing pipe 26 and the reaction liquid discharge line 28, a back-pressure regulating valve 27 was provided.

Into the reaction liquid collecting container 29, hydrochloric acid (of not less than 100 mol % of triethylamine to be introduced) for quenching triethylamine was introduced in advance. Moreover, to the reaction liquid collecting container 29, an exhaust vent 70 was connected. Further, the mixer 23 and the tubular reactor 25 was immersed in a water bath whose temperature had been adjusted to 30° C. The pressure inside of the reaction system was 0.4 MPa.

This reaction apparatus was used to produce HBN by reacting propionaldehyde with liquefied hydrogen cyanide in the presence of triethylamine. The length of the tubular reactor 25 and the flow rates of the raw materials transferred by the pumps 10 and 11 were changed so that the average residence time of reaction liquids in the tubular reactor 25 varied from 7 to 15 seconds (average residence time to the reaction liquid collecting container: 45 to 90 seconds) and the molar ratio of the raw materials supplied (i.e., the molar ratio of propionaldehyde to hydrogen cyanide) was 1.04:1.00, whereby the reaction yield of HBN in different reaction conditions was examined. HBN produced by each separate reaction was collected in the reaction liquid collecting container 29. A reaction liquid was analyzed in each separate condition, whereby the reaction yield of HBN was obtained. The results are shown in Table 2.

TABLE 2

| Reaction Condition | Average residence time (seconds) | HCN/nPA (mol/mol) | Water bath temperature (° C.) | Pressure inside of the system (MPa) | HBN yield (mol %) |
|---|---|---|---|---|---|
| 12 | 7 | 1.04 | 30 | 0.4 | 99 |
| 13 | 15 | 1.04 | | | 98 |

In Table 2, the molar ratio of propionaldehyde (nPA) to hydrogen cyanide (HCN) is denoted by HCN/nPA (mol/mol). In Reaction Conditions 12 and 13 listed in Table 2, the amounts of HBN production were 30 g/min and 15 g/min in Reaction Conditions 12 and 13, respectively. The temperature of the reaction liquid was 150° C., 58° C., and 33° C. at an average residence time of approximately 0.5 to 1 second, 3 seconds, and 7 seconds, respectively. As shown in Table 2, even when the amount of HBN production was scaled up three to thirty times as compared with the amount of HBN produced in Example 1, the reaction yield of HBN was as high as 98 to 99 mol %, regardless of reaction condition such as average residence time.

Example 3

A reaction was performed in the same manner as in Example 2, except that the tubular reactor in the reaction apparatus used in Example 2 was replaced by a tube and shell heat exchanger (heat-exchanging section: outside diameter 0.72 mm, inside diameter 0.49 mm, length 196 mm, ×55 pieces; made of SUS316) having a jacket. The heat of the heat exchanger was removed by allowing water whose temperature had been adjusted to 10° C. to circulate through the jacket section. A reaction liquid was analyzed in each separate condition, whereby the reaction yield of HBN was obtained. The results are shown in Table 3.

TABLE 3

| Reaction Condition | Average residence time (seconds) | HCN/nPA (mol/mol) | Coolant water discharge temperature (° C.) | Pressure inside of the system (MPa) | HBN yield (mol %) |
|---|---|---|---|---|---|
| 14 | 5 | 1.04 | 62 | 0.4 | 98 |
| 15 | 10 | 1.04 | 100 | | 97 |

In Table 3, the molar ratio of propionaldehyde (nPA) to hydrogen cyanide (HCN) is denoted by HCN/nPA (mol/mol). In Reaction Condition 14 listed in Table 3, the flow rate of the coolant water was 100 mL/min and the amount of HBN production was 30 g/min. Further, in Reaction Condition 15, the flow rate of the coolant water was 25 mL/min and the amount of HBN production was g/min. In Reaction Conditions 14 and 15, the temperature of the reaction liquid was 150° C. and 17° C. at an average residence time of approximately 0.5 seconds and 5 seconds, respectively. The discharge temperature of the coolant water used to remove the heat of the heat exchanger was 62° C. in Reaction Condition 14, and the coolant water boiled at 100° C. in Reaction Condition 15.

In the present example, the heat of the reaction liquid was sufficiently removed because the heat exchanger was used in performing the reaction. Moreover, as shown in Table 3, the reaction yield of HBN was as high as 97 to 98 mol %.

Example 4

In the present example, HBN was produced by use of such a reaction apparatus as shown in FIG. 1. In the present example, as the tubular reactor 25, a tube (outside diameter ⅛ in., inside diameter 2.17 mm; made of SUS316) having a jacket was used. Moreover, the amount of HBN production was further scaled up.

To a liquefied hydrogen cyanide cylinder (not shown) and a pump (C-610; manufactured by BUCHI) 10, an introducing pipe (outside diameter ⅛ in., inside diameter 2.17 mm; made of SUS316) 16 was connected for liquefied hydrogen cyanide to be introduced. The cylinder was pressurized at approximately 3 kg/cm$^2$ with nitrogen so that the hydrogen cyanide was prevented from being vaporized by pump suction. Further, to a pump (C-610; manufactured by BUCHI) 11, an introducing pipe (outside diameter ⅛ in., inside diameter 2.17 mm; made of SUS316) 16 was connected for propionaldehyde (with a purity of not less than 98%) to be introduced. In the propionaldehyde, 0.6 mol % of triethylamine had been dissolved in advance as a catalyst.

Furthermore, in order for the liquefied hydrogen cyanide to be introduced into the mixer (⅛ in., three-way union; manufactured by Swagelok) 23, the pump 10 and the mixer 23 were connected through a tube (outside diameter ⅛ in., inside diameter 2.17 mm) made of SUS316. Similarly, in order for the propionaldehyde to be introduced into the mixer 23, the pump 11 and the mixer 23 were connected through a tube (outside diameter ⅛ in., inside diameter 2.17 mm) 22 made of SUS316.

Further, to an outlet of the mixer, the tube (outside diameter ⅛ in., inside diameter 2.17 mm; made of SUS316) having a jacket was connected to serve as the tubular reactor 25. The tubular reactor 25 had thermocouples so provided in several places thereon as to monitor the temperature of a reaction liquid. The heat of the tubular reactor 25 was removed by allowing brine (an aqueous solution of ethylene glycol) cooled down to 0° C. to circulate through the jacket section of the tubular reactor 25. To the tubular reactor 25, a reaction liquid collecting container 29 was coupled through an introducing pipe 26 and a reaction liquid discharge line 28; and between the introducing pipe 26 and the reaction liquid discharge line 28, a back-pressure regulating valve 27 was provided. The reaction liquid collecting container 29 was a 200-liter collecting container (made of SUS304) having toluene introduced in advance thereinto for stirring. The pressure inside of the reaction system varied from 0.5 to 0.6 MPa.

This reaction apparatus was used to produce HBN by reacting propionaldehyde with liquefied hydrogen cyanide in the presence of triethylamine. The length of the tubular reactor 25 and the flow rates of the raw materials transferred by the pumps 10 and 11 were changed so that the average residence time of a reaction liquid in the tubular reactor 25 was 10 seconds and the molar ratio of the raw materials supplied (i.e., the molar ratio of propionaldehyde to hydrogen cyanide) was 1.04:1.00, whereby the reaction yield of HBN was examined.

The HBN/toluene solution produced by the reaction was collected in a collecting container into which hydrochloric acid (of not less than 100 mol % of triethylamine to be introduced) for quenching triethylamine had been introduced in advance. The reaction liquid thus collected was analyzed, whereby the reaction yield of HBN was obtained. The results are shown in Table 4.

TABLE 4

| Reaction Condition | Average residence time (seconds) | HCN/nPA (mol/mol) | Coolant water discharge temperature (° C.) | Pressure inside of the system (MPa) | HBN yield (mol %) |
|---|---|---|---|---|---|
| 16 | 10 | 1.04 | 62 | 0.5~0.6 | 96 |

In Table 4, the molar ratio of propionaldehyde (nPA) to hydrogen cyanide (HCN) is denoted by HCN/nPA (mol/mol). In Reaction Condition 16 listed in Table 4, the amount of HBN production was 180 g/min and the flow rate of the brine, which was used as coolant water, was 600 g/min. Further, the temperature of the reaction liquid was 130° C. at an average residence time of approximately less than 0.5 seconds and 2° C. at an average residence time of approximately 10 seconds. As shown in Table 4, even when the amount of HBN production was scaled up approximately not less than thirty times as compared with the amount of HBN produced in Example 1, the reaction yield of HBN was as high as 96 mol %.

Example 5

In the present example, lactonitrile was produced by use of such a reaction apparatus as shown below. In the present example, first, 22.0 g of 1.0 mol % TEA/acetoaldehyde (0.49 mol aldehyde) and 14.8 g of liquefied hydrogen cyanide (0.55 mol) were introduced into different syringes. For the prevention of vaporization of the raw materials, the syringes were cooled down by winding, around the syringes, small-diameter tubes having a refrigerant of 0 to 10° C. circulated therethrough.

The syringes, into which the respective raw materials had been introduced, were connected to a mixer (1/16 in., SUS316 Union Tee; manufactured by Swagelok). This mixer was connected to a tubular reactor (outside diameter 1/16 in., inside diameter 1.0 mm, length 100 cm; made of SUS316) that served also as a heat exchanger. Moreover, a 100-milliliter four-neck flask was connected to the tubular reactor through a reaction liquid introducing pipe (outside diameter 1/16 in., inside diameter 1.0 mm, length 65 cm; made of SUS316). This four-neck flask was equipped with a thermometer, a reflux condenser, and a stirrer.

The tubular reactor was immersed in a water bath whose temperature had been adjusted to approximately 30° C., and the four-neck flask was immersed in a water bath whose temperature had been adjusted to approximately 10° C. Then, a syringe pump was activated to supply TEA/acetoaldehyde at 0.23 ml/min and hydrogen cyanide at 0.17 ml/min (hydrogen cyanide:acetoaldehyde=1.12:1.00). The reaction liquid was collected in the four-neck flask, and left there for approximately two hours. The reaction liquid was analyzed by HPLC, whereby the reaction yield of lactonitrile was calculated to be as high as 99 mol %.

Example 6

In the present example, mandelonitrile was produced by use of such a reaction apparatus as shown below. In the present example, first, 25.0 g of 1.0 mol % TEA/benzaldehyde (0.23 mol aldehyde) and 9.6 g of liquefied hydrogen cyanide (0.35 mol) were introduced into different syringes. For the prevention of vaporization of the raw materials, the hydrogen cyanide syringe was cooled down by winding, around the syringe, a small-diameter tube having a refrigerant of 0 to 10° C. circulated therethrough.

The syringes, into which the respective raw materials had been introduced, were connected to a mixer (1/16 in., SUS316 Union Tee; manufactured by Swagelok). This mixer was connected to a tubular reactor (outside diameter 1/16 in., inside diameter 1.0 mm, length 100 cm; made of SUS316) that served also as a heat exchanger. Moreover, a 100-milliliter four-neck flask was connected to the tubular reactor through a reaction liquid introducing pipe (outside diameter 1/16 in., inside diameter 1.0 mm, length 65 cm; made of SUS316). This four-neck flask was equipped with a thermometer, a reflux condenser, and a stirrer.

The tubular reactor was immersed in a water bath whose temperature had been adjusted to approximately 30° C., and the four-neck flask was immersed in a water bath whose temperature had been adjusted to approximately 20° C. Then, a syringe pump was activated to supply TEA/acetoaldehyde at 0.20 ml/min and hydrogen cyanide at 0.12 ml/min (hydrogen cyanide:benzaldehyde=1.12:1.00). The reaction liquid was collected in the four-neck flask, and left there for approximately two hours. The reaction liquid was analyzed by HPLC, whereby the reaction yield of mandelonitrile was calculated to be as high as 97 mol %.

Example 7

Into a 500-milliliter four-neck flask equipped with a thermometer, a reflux condenser, and a stirrer, 188.0 g of the HBN reaction liquid obtained in Example 4 (HBN yield 96%, 1.0 mol scale-aldehyde) were fed. After the addition of 100.7 g of methanol (3.15 mol) and 19.5 g of water (1.08 mol), the internal temperature was adjusted to 20° C. After blowing of 43.7 g of hydrogen chloride (1.20 mol) maintained at 38±2° C. and then eight hours of reflux maturation, an α-hydroxybutanoic ester reaction liquid was obtained. The yield was analyzed by gas chromatograph with toluene held constant, and found to be 85.2 mol %.

Reference Example 1

HBN was produced through the batch process by using, as a reactor, a 3.5 m$^3$ glass lining reaction pot including a thermometer, a reflux condenser, and a stirrer. Into this reactor, 1210.6 kg of propionaldehyde (20.8 kmol) (with a purity of not less than 98%) and 11.2 kg of triethylamine (0.11 kmol) as a catalyst were introduced, and then cooled down to approximately 10° C. while being stirred. While the temperature inside of the reactor was kept at approximately 10 to 20° C. by cooling down the reactor as much as possible with use of brine of approximately −18° C., 587.1 kg of hydrogen cyanide (21.7 kmol) were dropped into the reactor over an eighteen-hour period. The resultant reaction liquid was analyzed, whereby the reaction yield of HBN was found to be 85 mol %.

Reference Example 2

HBN was produced through the batch process by using, as a reactor, a 300-milliliter four-neck flask including a thermometer, a reflux condenser, a stirrer, and a dropping funnel. Into this reactor, 145.2 g of propionaldehyde (2.50 mol) (with a purity of not less than 98%) and 1.5 g of triethylamine (15 mmol) as a catalyst were introduced, and then cooled down to approximately 15° C. while being stirred. While the temperature inside of the reactor was kept at 10 to 20° C., 23.5 g of hydrogen cyanide (0.87 mol) were dropped into the reactor over a forty-minute period. After the temperature was held within the range for 23 hours, 46.9 g of hydrogen cyanide (1.74 mol) were further dropped into the reactor over an eighty-minute period. The resultant reaction liquid was analyzed, whereby the reaction yield of HBN was found to be 87 mol %.

Reference Example 3

HBN was produced through the batch process by using, as a reactor, a 300-milliliter four-neck flask including a thermometer, a reflux condenser, a stirrer, and a dropping funnel. Into this reactor, 145.2 g of propionaldehyde (2.50 mol) (with a purity of not less than 98%) and 1.5 g of triethylamine (15 mmol) as a catalyst were introduced, and then cooled down to 25° C. while being stirred. While the temperature inside of the reactor was kept at 20 to 30° C., 23.5 g of hydrogen cyanide (0.87 mol) were dropped into the reactor over a thirty-minute period. After the temperature was held within the range for nineteen hours, 46.9 g of hydrogen cyanide (1.74 mol) were further dropped into the reactor over an eighty-minute period. The resultant reaction liquid was analyzed, whereby the reaction yield of HBN was found to be 79 mol %.

Reference Example 4

Into a 100-milliliter four-neck flask including a thermometer, a reflux condenser, a dropping funnel, and a stirrer, 42.4 g of benzaldehyde (0.40 mol) and 0.2 g of triethylamine (1.6 mmol, 0.4 mol % with respect to aldehyde) as a catalyst were fed, and then cooled down to not higher than 20° C. while stirring. While the temperature inside of the reactor was kept at 20 to 30° C., 3.8 g of hydrogen cyanide (0.14 mol) were dropped over a ten-minute period. After that, a temperature of 25° C. was kept for 22 hours. On this occasion, a crystal considered to be a by-product was found in the reaction liquid. After that, 7.6 g of hydrogen cyanide (0.29 mol) were dropped over a thirty-minute period. The resultant reaction liquid was analyzed, whereby the reaction yield of mandelonitrile was found to be 83 mol %.

Reference Example 51

Lactonitrile was produced through the batch process by using, as a reactor, a 200-milliliter four-neck flask including a thermometer, a reflux condenser, dropping funnel, and a stirrer. Into this reactor, 44.1 g of acetoaldehyde (1.00 mol) and 1.0 g of triethylamine (10 mmol, 1.0 mol % with respect to aldehyde) as a catalyst were fed, and then cooled down to 10° C. while being stirred. While the temperature inside of the reactor was kept at 0 to 10° C., 8.5 g of hydrogen cyanide (0.31 mol) were dropped into the reactor over a 25-minute period. After a temperature of 10° C. was kept for fifteen hours, 19.9 g of hydrogen cyanide (0.73 mol) were dropped into the reactor over a sixty-minute period. The resultant reaction liquid was analyzed, whereby the reaction yield of lactonitrile was found to be 61 mol %.

Reference Example 6

A reaction liquid containing α-hydroxybutanoic ester was obtained in the same manner as in Example 7, except that the reaction liquid obtained in Reference Example 1 was used. The reaction liquid was analyzed in the same manner, whereby the reaction yield of α-hydroxybutanoic ester based on the amount of propionaldehyde was found to be 76.0 mol %.

As shown by comparing Examples 1 to 7 and Reference Examples 1 to 6, it was confirmed that the production process according to the present invention can produce a desired cyanohydrin compound in good yield in each case. Further, as shown by comparing Example 7 and Reference Example 6, it was confirmed that the present example can produce an α-hydroxyester compound in good yield.

A process according to the present invention for producing a cyanohydrin compound flow-reacts a carbonyl compound such as an aldehyde compound with hydrogen cyanide, and can therefore achieve a reduction in residence time. This makes it possible to reduce the period of time over which the resulting cyanohydrin compound is exposed to an unreacted portion of the carbonyl compound such as the aldehyde compound, and to therefore produce the cyanohydrin compound in good yield by preventing the resulting cyanohydrin compound from reacting with the unreacted portion.

Further, a process according to the present invention for producing an α-hydroxyester compound makes it possible produce an intermediate, i.e. a cyanohydrin compound in good yield, considered in relation to a starting material, i.e. a carbonyl compound such as an aldehyde compound, and to therefore produce a final product, i.e. an α-hydroxyester compound in good yield.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

Industrial Applicability

A cyanohydrin compound produced by a production process according to the present invention is useful as a starting material for various compounds, and the present invention makes it possible to produce a cyanohydrin compound in good yield. Therefore, the present invention is widely applicable in the pharmaceutical industry, the agrichemical industry, and the like.

The invention claimed is:

1. A process for producing a cyanohydrin compound from a carbonyl compound (excluding a deuteride) and hydrogen cyanide,
   the process comprising the step of performing a flow reaction between the carbonyl compound and the hydrogen cyanide in the presence of a catalyst in a tubular reactor,
   wherein the tubular reactor has a fluid channel whose short side ranges from 0.01 mm to 15 mm in length,
   wherein a residence time during the flow reaction is less than 500 seconds, and
   wherein the catalyst is at least either an organic basic compound or an inorganic basic compound.

2. The process as set forth in claim 1, wherein the carbonyl compound is an aldehyde compound represented by general formula (1):

[Chem. 1]

(1)

wherein $R_1$ is an aryl group or a C1-C10 hydrocarbon group; and $R^1$ is allowed to have a substituent therein and to contain an atom other than carbon in a structure thereof.

3. The process as set forth in claim 1, wherein the hydrogen cyanide is flow-reacted in a proportion of 0.9 to 3.0 mol with respect to 1mol of the carbonyl compound.

4. A process for producing a cyanohydrin compound from a carbonyl compound (excluding a deuteride) and hydrogen cyanide,
   the process comprising the step of performing a flow reaction between the carbonyl compound and the hydrogen cyanide in the presence of a catalyst in a tubular reactor,
   wherein the tubular reactor has a fluid channel whose short side ranges from 0.01 mm to 15 mm in length,
   wherein a residence time during the flow reaction is less than 500 seconds, and
   wherein the catalyst is a compound selected from the group consisting of an amine compound, an aromatic amine compound, an alkali metal compound, a metal alkoxide compound, and an alkaline-earth metal compound.

5. The process as set forth in claim 1, wherein the flow reaction is performed in the presence of 0.001 to 0.1 mol of the catalyst with respect to 1 mol of the hydrogen cyanide.

6. The process as set forth in claim 4, wherein the carbonyl compound is an aldehyde compound represented by general formula (1):

[Chem. 1]

(1)

wherein $R^1$ is an aryl group or a C1-C10 hydrocarbon group; and $R^1$ is allowed to have a substituent therein and to contain an atom other than carbon in a structure thereof.

7. The process as set forth in claim 4, wherein the hydrogen cyanide is flow-reacted in a proportion of 0.9 to 3.0 mol with respect to 1 mol of the carbonyl compound.

8. The process as set forth in claim 4, wherein the flow reaction is performed in the presence of 0.001 to 0.1 mol of the catalyst with respect to 1 mol of the hydrogen cyanide.

* * * * *